United States Patent [19]

Warnant et al.

[11] 3,980,687

[45] Sept. 14, 1976

[54] INTERMEDIATES FOR THE PREPARATION OF 17-SUBSTITUTED-Δ⁴-GONENES

[75] Inventors: Julien Warnant, Neuilly-sur-Seine; Jean Jolly, Clichy-sous-Bois; Robert Joly, Montmorency, all of France

[73] Assignee: Roussel-UCLAF, Romainville, France

[22] Filed: July 18, 1974

[21] Appl. No.: 489,616

Related U.S. Application Data

[60] Division of Ser. No. 267,364, June 29, 1972, Pat. No. 3,843,686, which is a division of Ser. No. 63,277, Aug. 12, 1970, Pat. No. 3,702,334, which is a continuation-in-part of Ser. No. 640,507, May 23, 1967, Pat. No. 3,591,606.

[30] Foreign Application Priority Data

May 26, 1966 France .............................. 66.63086
Aug. 30, 1966 France .............................. 66.74629

[52] U.S. Cl. ........................ 260/488 B; 260/239.5; 260/295.5 T; 260/340.9; 260/347.5; 260/397.1; 260/397.3; 260/397.4; 260/410; 260/468 H; 260/468 R; 260/473 G; 260/476 C; 260/483; 260/486 R; 260/586 E; 260/611 F

[51] Int. Cl.² ................ C07C 69/145; C07C 69/24; C07C 69/61; C07C 69/74

[58] Field of Search ......... 260/488 B, 586 E, 476 C, 260/468 H, 468 R, 410, 486 R, 473 G, 483

[56] References Cited

UNITED STATES PATENTS 3,119,841  1/1964  Nomine et al.................. 260/488 B
3,880,911  4/1975  Saucy............................ 260/488 B

OTHER PUBLICATIONS

Chem. Abstracts, 56: 10235 g.
Chem. Abstracts, 58: 12635 d.
Chem. Abstracts, 61: 16130 a.

*Primary Examiner*—Vivian Garner
*Attorney, Agent, or Firm*—Hammond & Littell

[57] ABSTRACT

A process for the production of a Δ⁴-gonenic steroid having the formula

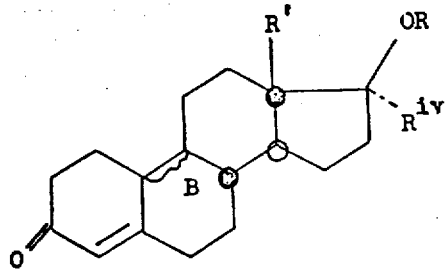

wherein R represents a member selected from the group consisting of hydrogen and the acyl of an organic carboxylic acid having from 1 to 18 carbon atoms, R' represents an alkyl having from 1 to 4 carbon atoms, R$^{iv}$ represents a member selected from the group consisting of lower alkyl, lower alkenyl or lower alkynyl, and B represents a member selected from the group consisting of two hydrogens in the 9α and 10β position and a double bond which comprises the steps of reacting a 3-ketal-4,5-seco-gonane-5-one with a ketalizing agent, oxidizing the resultant 3,5-diketal-4,5-seco-gonane-17β-ol, reacting the resultant 3,5-diketal-4,5-seco-gonane-17-one with an organometallic compound, hydrolyzing the resultant 3,5-diketal-17α-R$^{iv}$-4,5-seco-gonane-17β-ol, cyclizing the resultant 17α-R$^{iv}$-4,5-seco-gonane-17β-ol-3,5-dione and recovering said Δ⁴-gonenic steroid. The novel intermediates are also part of the invention. The Δ⁴-gonenic steroids are known compounds having steroidal properties.

4 Claims, No Drawings

3,980,687

1

INTERMEDIATES FOR THE PREPARATION OF 17-SUBSTITUTED-Δ⁴-GONENES

REFERENCE TO PRIOR APPLICATIONS

This application is a division of copending application Ser. No. 267,364, filed June 29, 1972, U.S. Pat. No. 3,843,686, which in turn is a division of application Ser. No. 63,277, filed Aug. 12, 1970, U.S. Pat. No. 3,702,334, which in turn is a continuation in part of application Ser. No. 640,507, filed May 23, 1967, U.S. Pat. No. 3,591,606.

THE PRIOR ART

It is a well known fact that the preparation of 19-nor steroids substituted in the 17-position presents difficult problems due to the presence of the functions on the steroid molecule apt to be attacked at the very moment of the introduction of the desired substituent in the 17-position. This is the case, in particular, with steroids having a ketone function in the 3-position and/or double bond in the 4,5-position.

Moreover, it is known that in the former processes for the preparation of steroid derivatives by means of total synthesis, the authors have, as a rule, preferred to complete the construction of the steroid skeleton first, and only then to proceed with the substitution in the 17-position (see, for example, Velluz et al, "Recent Advances in the Total Synthesis of Steroids", Angew. Chem. Intern, Edit., Vol. 4 [1965] No. 3).

OBJECTS OF THE INVENTION

An object of the present invention is the development of a process to form a steroid substituted in the 17-position from a steroid intermediate which can undergo substitution in the 17-position and thereafter total synthesis steps.

Another object of the present invention is the development of a process for the production of a Δ⁴-gonenic steroid of the formula

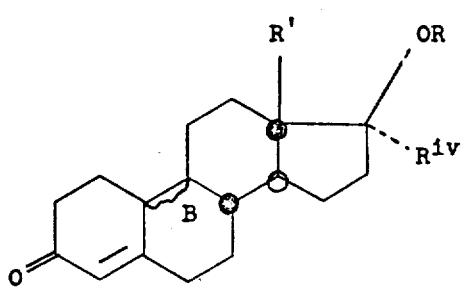

wherein R represents a member selected from the group consisting of hydrogen and the acyl of an organic carboxylic acid having from 1 to 18 carbon atoms, R' represents an alkyl having from 1 to 4 carbon atoms, R$^{iv}$ represents a member selected from the group consisting of lower alkyl, lower alkenyl and lower alkynyl, and B represents a member selected from the group consisting of two hydrogens in the 9α and 10β position and a double bond, which comprises (1) reacting a 4,5-seco-gonane-5-one of the formula

2

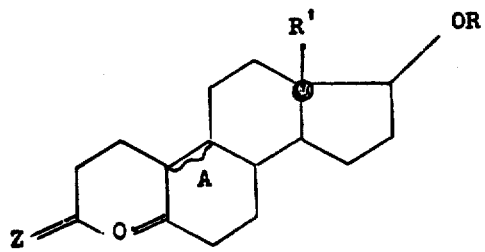

wherein R and R' have the above-assigned meanings, Z is a member selected from the group consisting of oxygen,

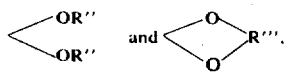

wherein R'' is lower alkyl and R''' is selected from the group consisting of lower alkylene and substituted lower alkylene, and A is selected from the group consisting of two hydrogens and a double bond, with a ketalization agent under ketalizing conditions, (2) saponifying the resultant 3,5-diketals of 4,5-seco-gonane-3,5-diones of the formula

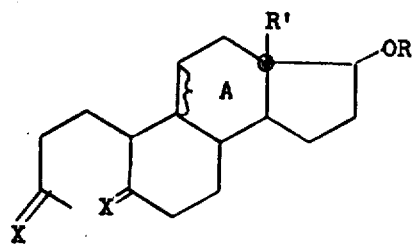

where X is a member selected from the group consisting of

wherein R'' and R''' have the above-assigned meanings, R', and A have the above-assigned meanings, and R is the acyl of an organic carboxylic acid having from 1 to 18 carbon atoms, by the action of an alkaline saponifying agent, (3) oxidizing the resultant 3,5-diketals of 4,5-seco-gonane-17β-ol-3,5-diones of the formula

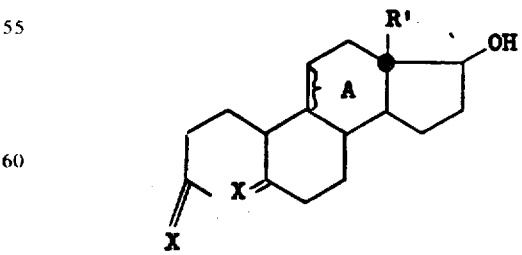

wherein R', X and A have the above-assigned meanings by the action of an hydroxyl oxidizing agent, (4) reacting the resultant 3,5-diketals of 4,5-seco-gonane-3,5,17-triones of the formula

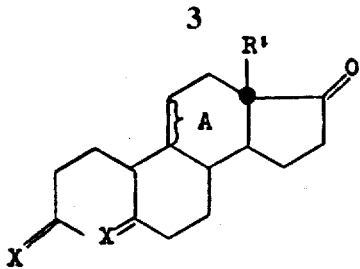

wherein R', X and A have the above-assigned meanings with an organometallic compound of the formula selected from the group consisting of $R^{iv}Li$ and $R^{iv}MgX$, wherein $R^{iv}$ has the above-assigned meaning and X represents a halogen, (5) recovering the resultant 3,5-diketals of $17\alpha$-$R^{iv}$-4,5-seco-gonane-3,5-diones of the formula

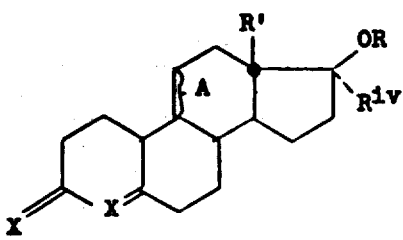

wherein R, R', $R^{iv}$, X and A have the above-assigned meanings, (6) hydrolyzing said compounds by the action of a ketal hydrolyzing agent in the presence of an organic solvent, (7) subjecting the resultant $17\alpha$-$R^{iv}$-4,5-seco-gonane-3,5-diones of the formula

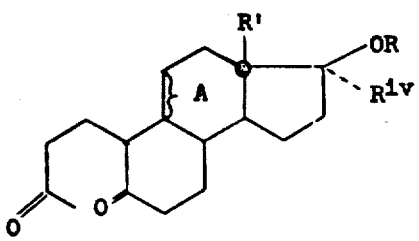

wherein R, R', $R^{iv}$ and A have the above-assigned meanings to the action of a cyclizing agent selected from the group consisting of acid and basic cyclization agents, and (8) recovering said $\Delta^4$ gonenic steroid.

A further object of the present invention is the obtention of the novel intermediates: the 3,5-diketals of $17\alpha$-$R^{iv}$-4,5-seco-gonane-3,5-diones; and the $17\alpha$-$R^{iv}$-4,5-seco-gonane-3,5-diones.

These and other objects of the present invention will become more apparent as the description thereof proceeds.

DESCRIPTION OF THE INVENTION

It has now been discovered that a novel class of intermediate products for the synthesis of steroid derivatives, namely, the 3,5-diketals of $13\beta$-alkyl-4,5-seco-gonane-3,5,17-triones of the general formula given in the above, permit, in contrast to the 3-monoketals already known, to bypass the difficulties previously met with in the preparation of 19-nor steroids substituted in the 17 position, due to the possibility of introducing at this stage the desired substituents in the 17 position.

The 3,5-diketals of the $13\beta$-alkyl-4,5-seco-gonane-3,5,17-triones thus formed show in neutral or alkaline medium an excellent stability with regard to the functions in the 3 and 5 positions, which facilitates the possible conversions in the 17 position. Moreover, they are, after splitting off the ketal functions in the 3 and 5 positions, easily cyclized by the usual agents to give the tetraacyclic steroid skeleton.

The present invention relates to a new class of intermediate products for the synthesis of steroid derivatives as well as to a process for the preparation of these products.

More particularly, the invention relates to the 3,5-diketals of the $13\beta$-alkyl-$17\alpha$-$R^{iv}$-$17\beta$-OR-4,5-seco-gonane-3,5-diones of the general formula I

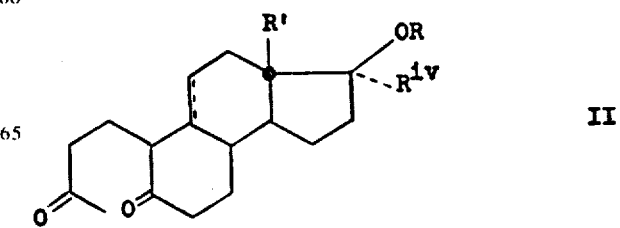

wherein, here and in the following, R represents hydrogen or the acyl of an organic carboxylic acid having 1 to 18 carbon atoms, R' is an alkyl radical containing 1 to 4 carbon atoms, X represents the group $$\diagdown\mkern-10mu\diagup^{OR''}_{OR''}$$

R'' being a lower alkyl, or X represents the group $$\diagdown\mkern-10mu\diagup^{O}_{O}\!\!\diagdown\mkern-10mu R'''.$$

R''' being a lower alkylene radical, substituted or unsubstituted, $R^{iv}$ represents lower alkyl, lower alkenyl or lower alkynyl, and the dashed line represents a possible 9(11) double bond; and the $13\beta$-alkyl-$17\alpha$-$R^{iv}$-$17\beta$-OR-4,5-seco-gonane-3,5-diones of the general formula II

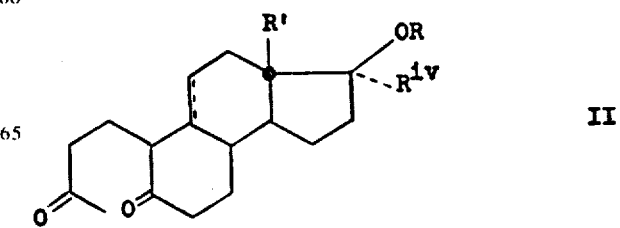

wherein R, R' and R'' have the above-assigned meanings.

The process for the preparation of Δ⁴-gonenic steroids of the general formula III, also object of the present invention,

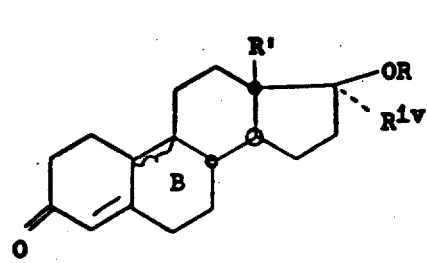

wherein R, R' and R'' have the above-assigned meanings and B is a double bond or two hydrogens in the 9α and 10β position, is characterized in that a 3-Z-13β-alkyl-17β-OR-4,5-seco-gonane-5-one of the general formula IV

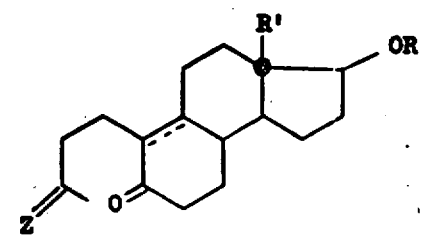

wherein Z represents a ketone oxygen or X, R, R' and X having the above-assigned meanings, and the dashed line represents a possible 9(10) double bond, is subjected to the action of a ketalization agent, the diketal obtained of the general formula V

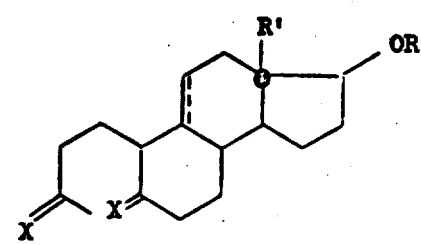

wherein X, R, R' and the dashed line have the above-assigned meanings, when R represents the radical of an organic carboxylic acid having from 1 to 18 carbon atoms, is saponified, and the diketal of the general formula VI

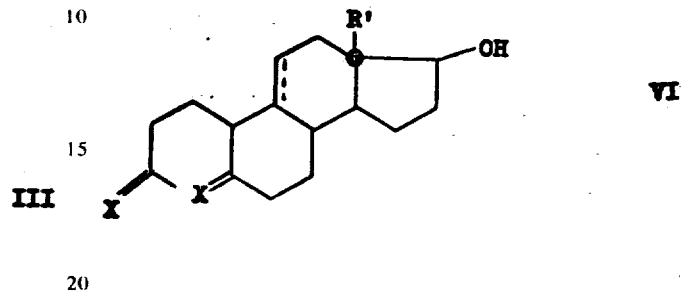

wherein X, R' and the dashed line have the above-assigned meanings, is reacted with an oxidizing agent. The resulting 3,5-diketal of 13β-alkyl-4,5-seco-gonane-3,5,17-trione of the general formula VII

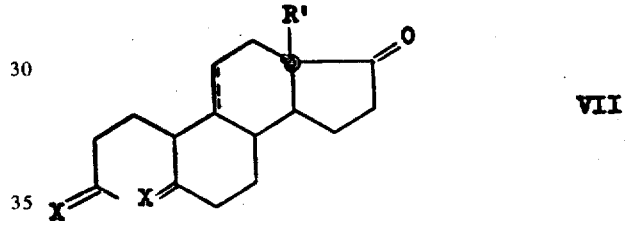

wherein R' and X have the above-assigned meanings, is isolated.

The process, also object of the invention, can be advantageously executed as follows:

A. The ketalization agent is chosen from the group consisting of the lower cyclic ketals, the lower non-cyclic ketals and the lower alkanols. The work is conducted in the presence of an acid catalyst.

B. The cyclic ketals are chosen from the group consisting of 2-methyl-2-ethyl-dioxolane, 2-methyl-2-phenyl-dioxolane, 2-methyl-4-(6-methylbenzyl)-dioxolane, 2,2-dimethyl-4-(6-methylbenzyl)-dioxolane, 2-chloromethyldioxolane, 2-(β-chloro)-ethyl-dioxolane and 2-(β-bromo)-ethyl-dioxolane.

C. The non-cyclic ketals are selected from the group consisting of the dimethyl ketal of acetone, the diethyl ketal of acetone, the dimethyl ketal of 2-butanone, the dimethyl ketal of dimethylformamide and the diethyl ketal of dimethylformamide.

D. The aliphatic alcohols employed as ketalizing agents are chosen from the group consisting of glycols such as lower alkanediols, for example, ethyleneglycol, 1,3-propanediol, 2,2-dimethyl-1,3-propanediol, and of lower alkanols such as methanol or ethanol.

E. The saponification of the 3,5-diketal of 13β-alkyl-17β-acyloxy-4,5-seco-gonane-3,5-dione of the general formula V is effected by an alkaline agent such as an alkali metal hydroxide, for example, sodium or potassium hydroxide. The work is carried out in a lower alkanol such as methanol or ethanol.

F. The oxidation of the hydroxyl in the 17 position is realized according to the Oppenauer method by means of a lower aliphatic ketone such as lower alkanones, for example, acetone, methylethyl ketone, methylisobutyl ketone or lower cycloalkanones, for example, cyclohexanone, in the presence of an aluminum tertiary lower alkanolate such as aluminum isopropylate.

G. The oxidation of the hydroxyl in the 17 position is effected by using, as oxidizing agent, chromic acid anhydride in pyridine.

As it has already been mentioned, the advantages of the novel compounds of the general formula VII lie in particular in the fact that they allow an easy preparation of 19-nor steroids substituted in the 17 position, as it will be explained in the following.

The introduction of a substituent in the 17α position is realized, for example, by reaction of a compound of formula I with an organometallic compound of the type R'''Li or R'''MgX (X being a halogen and, in particular, bromine or iodine and R''' represents a hydrocarbon radical, preferably lower alkyl, lower alkenyl or lower alkynyl).

In the particular case of ethynylation, this reaction may be realized with the aid of an ethynyl magnesium halide or also with the aid of an alkali metal acetylide or also with the aid of acetylene while operating in the presence of tertiary alcoholates or amides of alkali metals or alkaline earth metals.

The introduction of the ethyl or vinyl radical in the 17α position can be effected with excellent yields in an indirect fashion in two steps. By ethynylation of the ketone in the 17 position and subsequent reduction of the ethynyl radical by hydrogenation in the presence of a catalyst having a platinum or palladium base, the 17α-ethyl derivative is obtained, whereas if the reduction is arrested after the absorption of a mol equivalent of hydrogen gas, the 17α-vinyl derivative is obtained.

The process of indirect introduction may furthermore be significant with regard to the preparation of the 17α-propyl derivatives. In that case, allyl magnesium bromide can be reacted with a compound of formula I, then the resultant allylic derivative is subjected to a hydrogenation in the presence of a catalyst having a platinum or palladium base.

The 3,5-diketals of the 13β-alkyl-17α-R'''-17β-hydroxy-4,5-seco-gonane-3,5-diones, possibly having a double bond in the 9(11) position (I, R=H), obtained by the above reactions, can be esterified in the 17 position with an organic carboxylic acid having from 1 to 18 carbon atoms by employing the usual acylation agents such as the corresponding acid, its anhydride or its chloride.

Such acids are the aliphatic or cycloaliphatic carboxylic acids, saturated or unsaturated, or the aromatic or heterocyclic carboxylic acids, for example, the alkanoic acids such as formic, acetic, propionic, butyric, isobutyric, valeric, isovaleric, trimethylacetic, caproic, β-trimethylpropionic, enanthio, caprylic, pelargonic, capric, undecylic, lauric, myristic, palmitic, stearic, etc., the alkenoic acids such as undecylenic, oleic, etc., the cycloalkyl carboxylic acids such as cyclopentyl-, cyclopropyl-, cyclobutyl- and cyclohexyl-carboxylic acids, the cycloalkylalkanoic acids such as cyclopropylmethyl carboxylic acid, cyclobutylmethyl carboxylic acid, cyclopentylethyl carboxylic acid, cyclohexylethyl carboxylic acid, the cyclopentylacetic, cyclohexylacetic, the phenylalkanoic acids such as phenylacetic or propionic acids, benzoic acid, the phenoxyalkanoic acids such as phenoxyacetic acids, p-chlorophenoxyacetic acid, 2,4-dichlorophenoxyacetic acid, 4-tert.-butyl-phenoxyacetic acid, 3-phenoxypropionic acid, 4-phenoxybutyric acid, the furane 2-carboxylic acids such as 5-tert.-butylfurane-2-carboxylic acid, 5-bromo-furane-2-carboxylic acid, the nicotinic acids, the β-ketoalkanoic acids, for example, the acetylacetic, propionylacetic, butyrylacetic acids, etc.

The 3,5-diketals of the 13β-R'-17α-R'''-17β-hydroxy-4,5-seco-gonane-3,5-diones with or without a 9(11) double bond, whether esterified or unesterified in the 17β position, can be subsequently converted into tetracyclic steroids.

For that purpose, such a 3,5-diketal of a 13β-R'-17α-R'''-17β-hydroxy- or 17β-acyloxy-4,5-seco-gonane-3,5-dione formed as indicated above is subjected to a ketal hydrolysis in the presence of an acid, such as citric, acetic, hydrochloric or sulfuric acid, and in the presence of one or several solvents such as an alcohol, for example, the methanol or ethanol, and a hydrocarbon such as benzene or toluene. In this manner the keto groups in the 3 and 5 positions are regenerated and the corresponding 3,5-dioxo derivative is recovered possibly having a double bond in the 9(10) position. Next, this 3,5-dioxo derivative is subjected to the action of a basic cyclization agent such as an alkali metal alcoholate, or to the action of an acid cyclization agent such as hydrochloric acid or the hydrochloric acid-acetic acid mixture.

Thus, a tetracyclic steroid of the general formula III

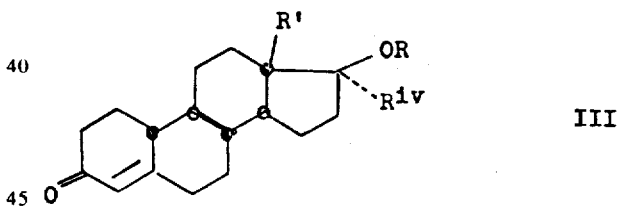

III wherein R, R' and R''' have the previous meanings, is obtained possibly with a double bond in the 9(10) position.

In the case where the cyclization agent is a secondary base such as, for example, pyrrolidine, the corresponding enamines are obtained in the 3-position, which by means of acid hydrolysis supply the above-indicated 3-oxo-Δ⁴ or 3-oxo-Δ⁴,⁹ derivatives.

By applying the methods described in the preceding, it is possible to prepare, starting with the compounds of the general formula I, physiologically active steroids such as, for example, 17α-ethynyl-19-nor-testosterone, 17α-ethyl-19-nor-testosterone, the acetate of 17α-ethynyl-19-nor-testosterone, 17α-ethynyl-Δ⁴,⁹-estradiene-17β-ol-3-one, 13β-ethyl-17α-ethynyl-Δ⁴-gonene-17β-ol-3-one, 13β,17α-diethyl-Δ⁴-gonene-17β-ol-3-one, 13β-ethyl-17α-ethynyl-Δ⁴,⁹-gonadiene-17β-ol-3-one and the corresponding 13β-n-propyl and 13β-n-butyl derivatives.

As it has been shown in the preceding, tetracyclic steroids of gonanic structure can be prepared by starting with the compounds of formula IV.

The starting compounds of the process of the invention are described and are accessible by application of the processes of French Pat. Nos. 1,243,000, 1,364,556, 1,476,509 and 1,432,569.

The following examples will serve for better comprehension of the invention. However, it is to be understood that they are not to be deemed limitative in any degree. The process described in the following can also be applied with the same readiness to the 13$\beta$-ethyl, 13$\beta$-propyl or 13$\beta$-butyl derivatives as to the 13$\beta$-methyl derivatives.

EXAMPLE I

Peparation of 3-ethylenedioxy-4,5-seco-estrane-17$\beta$-ol-5-one 900 cc of toluene, 18 cc of pyridine, 180 gm of 3-ethylenedioxy-4,5-seco-$\Delta^9$-estrene-17$\beta$-ol-5-one and 72 gm of palladized talc containing 2% of palladium, were introduced into a hydrogenation vessel. The vessel was purged and the mixture was agitated under an atmosphere of hydrogen at room temperature. Over a period of 6 hours about 12 liters of hydrogen were absorbed.

Thereafter, the reaction solution was filtered and 180 cc of water were added thereto. Next, the washing was effected, followed by decanting, first with an aqueous solution of normal sulfuric acid to eliminate the pyridine, then with an aqueous solution of sodium bicarbonate and finally with water until the wash waters were neutral. The toluene phase was dried over magnesium sulfate, concentrated to dryness under reduced pressure, thus obtaining 180 gm of raw 3-ethylenedioxy-4,5-seco-estrane-17$\beta$-ol-5-one. This product was used as such for the next step.

A sample of this product was purified for analysis by recrystallization from isopropyl ether containing 1 part per thousand of pyridine, then from ethyl ether containing 1 part per thousand of pyridine. It had a melting point of 80° to 85°C and a specific rotation $[\alpha]_D^{20} = +3° + 1°$ (c = 1% methanol containing 1% of pyridine), and it possessed the following characteristics:

Analysis: $C_{20}H_{32}O_4$; molecular weight = 336.46. Calculated: C, 71.39%; H, 9.59%. Found: C, 71.2%; H, 9.5%.

Infrared spectra (in chloroform):

Absorption at:

1,704 cm$^{-1}$: carbonyl 3,600 cm$^{-1}$: hydroxyl and C—O—C band, characteristic of the ketal function.

This product is not described in the literature.

The 3-ethylenedioxy-4,5-seco-$\Delta^9$-estrene-17$\beta$-ol-5-one, utilized as the starting product in the preceding preparation, was obtained in the course of the process described in French Pat. No. 1,364,556.

In an analogous manner, the 3-ethylenedioxy-13$\beta$-ethyl-4,5-seco-gonane-17$\beta$-ol-5-one was prepared by starting with the 3-ethylenedioxy-13$\beta$-ethyl-4,5-seco-$\Delta^9$-gonene-17$\beta$-ol-5-one, having a melting point of 95° to 100°C, this product being obtained in the course of the process described in the French Pat. No. 1,476,509. The 3-ethylenedioxy-13$\beta$-ethyl-4,5-seco-gonane-17$\beta$-ol-5-one is not described in the literature.

EXAMPLE II

Preparation of 3,5-bis-(ethylenedioxy)-4,5-seco-estrane-17-one

Step A: Preparation of 3,5-bis-(ethylenedioxy)-4,5-seco-estrane-17$\beta$-ol.

Under an inert atmosphere, first 70 gm of 3-ethylenedioxy-4,5-seco-estrane-17$\beta$-ol-5-one, then 0.35 gm of paratoluene sulfonic acid were introduced into 350 cc of methylethyldioxolane. The mixture was agitated for about 15 hours. Thereafter, the reaction mixture was made alkaline with 2.1 cc of pyridine, agitated for 10 minutes, then 126 cc of water and 14 cc of a saturated aqueous solution of sodium bicarbonate was added. The organic phase was separated by decanting and washed with water. The aqueous wash waters were extracted with benzene, which was washed with water, then combined with the organic phase previously isolated and washed. These combined organic phases were dried over magnesium sulfate and concentrated to dryness under reduced pressure. The residue was taken up in isopropyl ether and concentrated to dryness under reduced pressure. 84 gm of a raw product were recovered, which was crystallized from isopropyl ether, obtaining 69.7 gm of 3,5-bis-(ethylenedioxy)-4,5-seco-estrane-17$\beta$-ol.

The product had a specific rotation $[\alpha]_D^{20} = +18° + 1°$ (c = 1% in methanol containing 1% of pyridine).

By concentration of the mother liquors resulting from the crystallization, a second yield of product was obtained.

A sample of the product was purified for analysis from isopropyl ether containing 1 part per thousand of pyridine. It had a melting point of 90° to 100°C and a specific rotation $[\alpha]_D^{20} = +19° \pm 1°$ (c = 1% in methanol containing 1% of pyridine), and possessed the following characteristics:

Analysis: $C_{22}H_{36}O_5$; molecular weight = 380.50. Calculated: C,69.44%; H,9.53%. Found: C,69.1%; H,9.7%.

Infrared spectra (in chloroform):

Absorption at 3,600 cm$^{-1}$: hydroxyl and C—O—C band characteristic of the ketal function.

This product is not described in the literature.

Step B: Preparation of 3,5-bis-(ethylenedioxy)-4,5-seco-estrane-17-one

Under an inert atmosphere, 40 gm of purified 3,5-bis-(ethylenedioxy)-4,5-seco-estrane-17$\beta$-ol were dissolved in a mixture of 400 cc of toluene and 80 cc of methylethylketone in a 2-liter vessel equipped with an agitation means and a descending condenser. The solution was brought to boiling point under agitation. Then after distillation had been established, a solution of 14.4 gm of aluminum isopropylate in 540 cc of toluene and 720 cc of methylethylketone was introduced. This addition was effected as follows: The two reactants were introduced simultaneously at regular intervals for about 15 minutes and within a total time of 4 to 5 hours in such a manner that the evaporated solvent volume was proportionately compensated by the addition of the two reactants. Thus, within a space of about 4 to 5 hours, 1,260 cc of distillate were recovered. The distillation was continued until 80 cc of distillate were recovered. The reaction mixture was cooled. Next, 36 cc of water were introduced and the solution was agitated. The precipitated alumina was vacuum filtered. Water was added to the filtrate and the organic solvents were eliminated by steam distillation. The aqueous mixture was cooled and the precipitate formed was vacuum filtered, washed with water and dried. The recovered raw product was crystallized from methanol containing 1 part per thousand of pyridine, thus obtaining 30.8 gm of 3,5-bis-(ethylenedioxy)-4,5-seco-estrane-17-one. The product had a melting point of 114°C.

A sample of this product, purified for analysis by crystallization first from isopropyl ether containing 1 part per thousand of pyridine, then from methanol containing 1 part per thousand of pyridine, had a melting point of 114°C. and a specific rotation $[\alpha]_D^{20} = +75° \pm 1.5°$ (c = 1% in methanol containing 1% of pyridine), and had the following characteristics:

Analysis: $C_{22}H_{34}O_5$; molecular weight = 378.49. Calculated: C,69.81%; H,9.05%. Found: C,69.9%; H,8.9%.

Infrared spectra (in chloroform):

Absorption at 1,732 $cm^{-1}$: carbonyl and C—O—C band characteristic of the ketal function.

This product is not described in the literature.

EXAMPLE III

Preparation of
3,5-bis-(ethylenedioxy)-4,5-seco-estrane-17-one, starting with 4,5-seco-estrane-17β-ol-3,5-dione 10 gm of 4,5-seco-estrane-17β-ol-3,5-dione, a product described in French Pat. No. 1,432,569, were introduced into 60 cc of methylethyldioxolane. The mixture was brought to reflux under an inert atmosphere and 1 volume of solvent was distilled therefrom under normal pressure. The mixture was then cooled toward 75°C and 0.050 gm of paratoluene sulfonic acid was added. Under a slight vacuum, the mixture was distilled for 3 hours at about 75°C., recovering about 10 cc of distillate per hour and maintaining the reaction media at a constant volume by the addition of methylethyldioxolane. Thereafter, the methylethyldioxolane was eliminated under reduced pressure. The reaction media was cooled. 20 cc of benzene and 0.4 cc of pyridine were added to the reaction mixture, which was then homogenized and was, after 18 cc of water and 2 cc of a saturated solution of sodium bicarbonate had been added, agitated for 10 minutes. The benzenic phase was separated by decanting and washed with water. The aqueous phases were re-extracted with benzene. After having been washed with water, these benzenic re-extracts were combined with the principal benzenic solution. After the addition of one drop of pyridine, the whole of the combined benzenic solutions was concentrated to dryness under reduced pressure. The resultant residue was dissolved in hot ethyl ether. The ether was expelled under vacuum and the crystallizate was dried. 13.27 gm of a raw product were obtained, having a melting point of 90° to 100°C and a specific rotation $[\alpha]_D^{20} = +18° \pm 1°$ (c = 1% in methanol containing 1% of pyridine).

This raw product was recrystallized from isopropyl ether containing 1 part per thousand of pyridine, thus obtaining 8.75 gm of 3,5-bis-(ethylenedioxy)-4,5-seco-estrane-17β-ol, having a melting point of 90° to 100°C. with a specific rotation of $[\alpha]_D^{20} = +19.5° \pm 1°$ (c = 1% in methanol containing 1% of pyridine). This product was identical to the 3,5-bis-(ethylenedioxy)-4,5-seco-estrane-17β-ol prepared in Step A of the preceding example. By applying the process described in Step B of the preceding example to this compound, 3,5-bis-(ethylenedioxy)-4,5-seco-estrane-17-one was obtained, which was identical to the product prepared according to Example II.

EXAMPLE IV

Preparation of
3,5-bis-(ethylenedioxy)-4,5-seco-$\Delta^{9(11)}$-estrene-17-one

Step A: Preparation of
3,5-bis-(ethylenedioxy)-17β-benzoyloxy-4,5-seco-$\Delta^{9(11)}$-estrene.

Under an atmosphere of nitrogen, 2 gm of 17β-benzoyloxy-4,5-seco-$\Delta^9$-estrene-3,5-dione, having a specific rotation $[\alpha]_D^{20} = +43°$ (c = 1% in methanol), a product described in French Pat. No. 1,243,000, were introduced into 60 cc of methylethyldioxolane. 0.06 gm of paratoluene sulfonic acid monohydrate were added thereto, and the reaction mixture was heated under agitation in order to obtain within the space of 5 hours a volume of distillate of about 20 cc while maintaining the reaction volume constant by the regular addition of methylethyldioxolane. The pH was adjusted to 8.0 by the addition of an aqueous solution of sodium bicarbonate. The organic phase was separated by decanting, washed with water until neutrality was attained and dried. One drop of pyridine was added to the organic phase, which was then distilled to dryness under reduced pressure. Next, ethanol was added to the residue and the mixture was again concentrated to dryness under reduced pressure.

The resultant residue was crystallized from ethanol, thus obtaining 1.6 gm of 3,5-bis-(ethylenedioxy)-17β-benzoyloxy-4,5-seco-$\Delta^{9(11)}$-estrene. The product had a melting point of 165° to 166°C.

A sample of this product, recrystallized first from isopropyl ether in the presence of pyridine, then from ethanol also in the presence of pyridine, had the following constants: Melting point = 166° to 167°C Specific rotation = $[\alpha]_D^{20} = +23.2°$ (c = 0.9% in methanol).

Analysis: $C_{29}H_{38}O_6$; molecular weight = 482.6. Calculated: C, 72.17%; H, 7.93%. Found: C, 72.4%; H, 8.1%.

| Ultraviolet spectra (in ethanol): | |
|---|---|
| max. at 230 mμ | $\epsilon$ = 14,300 |
| max. at 273 mμ | $\epsilon$ = 910 |
| max. at 280 mμ | $\epsilon$ = 720 |

This product is not described in the literature.

Step B: Preparation of
3,5-bis-(ethylenedioxy)-4,5-seco-$\Delta^{9(11)}$-estrene-17β-ol Under an atmosphere of nitrogen, 600 mg of 3,5-bis-(ethylenedioxy)-17β-benzoyloxy-4,5-seco-$\Delta^{9(11)}$-estrene were introduced into 19 cc of a 0.158 N potassium hydroxide solution. The mixture was maintained at reflux for 1 hour, then concentrated to dryness under reduced pressure. Next, water was added to the mixture, which was then extracted with ether and the extracts were combined. The organic solution obtained was washed with water, dried and concentrated to dryness. After adding isopropyl ether, the solution was crystallized, vacuum filtered and dried. In this manner, 362 mg of 3,5-bis-(ethylenedioxy)-4,5-seco-$\Delta^{*(1)}$-estrene-17β-ol were obtained having a melting point of 130°C.

A sample of this product was purified by crystallization first from isopropyl ether, then from petroleum ether (boiling range = 60° to 80°C). The product had a melting point of 132°C and a specific rotation $[\alpha]_D^{20}$ = +25.8° (c = 0.7% in methanol).

Analysis: $C_{22}H_{34}O_5$; molecular weight = 378.49. Calculated: C, 69.81%; H, 9.05%. Found: C, 69.8%; H, 9.1%.

This product is not described in the literature.

Step C: Preparation of 3,5-bis-(ethylenedioxy)-4,5-seco-$\Delta^{*(1)}$-estrene-17-one Within a space of 10 minutes, about 1 gm of chromic acid, followed by a solution composed of 10 cc of pyridine and 1 gm of 3,5-bis-(ethylenedioxy)-4,5-seco-$\Delta^{*(1)}$-estrene-17β-ol were introduced into 10 cc of pyridine cooled to 0°C. This mixture was allowed to warm to a temperature of 20°C., then agitated for 15 hours at this temperature. Thereafter, the reaction mixture was poured into water and filtered. The aqueous phase was extracted with methylene chloride and the methylene chloride extracts were combined. The organic solution obtained was washed with water and dried, then concentrated to dryness under reduced pressure.

The residue was crystallized from isopropyl ether and 0.665 gm of 3,5-bis-(ethylenedioxy)-4,5-seco-$\Delta^{*(1)}$-estrene-17-one was obtained, having a melting point of 98°C.

A sample of this product was purified for analysis by crystallization from isopropyl ether. It had a melting point of 98°C. and a specific rotation $[\alpha]_D^{20}$ = +105° (c =0.5% in methanol).

Analysis: $C_{22}H_{32}O_5$; molecular weight = 376.46. Calculated: C, 70.18%; H, 8.56%. Found: C, 70.1%; H, 8.5%.

This product is not described in the literature.

EXAMPLE V
Preparation of 17α-ethynyl-19-nor-testosterone

Step A: Preparation of 3,5-bis-(ethylenedioxy)-17α-ethynyl-4,5-seco-estrane-17β-ol Under agitation, a stream of acetylene was allowed to bubble through 40 cc of a sodium tert.-amylate solution in toluene containing 2.28 gm of sodium per 100 cc for 2 hours. Thereafter, 5 gm of 3,5-bis-(ethylenedioxy)-4,5-seco-estrane-17-one (described in Step B of Example II) and 10 cc of toluene were introduced into the solution of sodium acetylide obtained. The mixture was then agitated for 3 hours and 30 minutes at room temperature while a stream of acetylene was bubbled therethrough. Next, the reaction mixture was cooled to about 15°C. under an inert atmosphere. A solution of 5 gm of ammonium chloride in 15 cc of water was introduced. The toluene was distilled under reduced pressure while maintaining the volume constant by addition of water, thus obtaining 5.28 gm of 3,5-bis-(ethylenedioxy)-17α-ethynyl-4,5-seco-estrane-17β-ol. The product had a melting point of 181° to 182°C. and was utilized as such for the next step.

A sample of this product, purified for analysis by recrystallization from methanol containing 1 part per thousand of pyridine, had a melting point of 183°C. and a specific rotation $[\alpha]_D^{20}$ = − 30° ± 2° (c = 1% in methanol containing 1% of pyridine) and possessed the following characteristics:

Analysis: $C_{24}H_{36}O_5$; molecular weight = 404.52. Calculated: C, 71.25%; H, 8.97%. Found: C, 71.4%; H, 9.0%.

| Infrared spectra (in chloroform): | | |
|---|---|---|
| Absorption at: | 3,300 cm$^{-1}$; | ethynyl |
| | 3,590 cm$^{-1}$; | hydroxyl |
| and C—O—C band characteristic of the ketal function. | | |

This product is not described in the literature.

Step B: Preparation of 17α-ethynyl-4,5-seco-estrane-17β-ol-3,5-dione

First, 1.5 gm of 3,5-bis-(ethylenedioxy)-17α-ethynyl-4,5-seco-estrane-17β-ol, then 1.5 gm of citric acid were introduced into a mixture of 7.5 cc of toluene, 3 cc of methanol and 3 cc of water. Under agitation and an inert atmosphere, the mixture was held at reflux for one hour. Then 15 cc of water were added thereto. The toluene was concentrated under reduced pressure. The precipitate formed was isolated by being vacuum filtered, washed with water until the wash waters were neutral and dried. Thus, 1.13 gm of 17α-ethynyl-4,5-seco-estrane-17β-ol-3,5-dione were obtained. The product had a melting point of 135° to 136°C. and it was utilized as such for the following step.

A sample of this product, purified for analysis by crystallization from ethyl ether, had a melting point of 135° to 136°C. and a specific rotation $[\alpha]_D^{20}$ = − 50.4° ± 2° (c = 1% in methanol) and had the following characteristics:

Analysis: $C_{20}H_{28}O_3$; molecular weight = 316.42. Calculated: C, 75.91%; H, 8.91%. Found: C, 76.0%; 8.9%.

| Infrared spectra (in chloroform): | | |
|---|---|---|
| Absorption at: | 1,703 cm$^{-1}$; | carbonyl |
| | 3,300 cm$^{-1}$; | ethynyl |
| | 3,590 cm$^{-1}$; | hydroxyl |

This product is not described in the literature.

Step C: Obtention of 17α-ethynyl-19-nor-testosterone

Under an inert atmosphere, 0.900 gm of 17α-ethynyl-4,5-seco-estrane-17β-ol-3,5-dione were introduced into a mixture of 9 cc of methanol and 2.7 cc of methylene chloride. The mixture was agitated for 15 minutes; then 1 cc of a methanolic solution of sodium methylate, containing 7.8 gm of sodium per 100 cc, was added, and the reaction mixture was agitated for 5 hours at room temperature. Thereafter, 0.3 cc of acetic acid and 10 cc of water were added. Next, the methanol and the methylene chloride were eliminated under reduced pressure, and the precipitate was vacuum filtered. In this way, 0.84 gm of 17α-ethynyl-19-nor-testosterone were obtained. The product had a melting point of 206°C. and a specific rotation $[\alpha]_D^{20}$ = −22.5° (c = 2% in chloroform).

After having been purified, a sample of this product had a melting point of 206.5° to 207°C and a specific rotation $[\alpha]_D^{20} = -24° \pm 2°$ (c = 1% in chloroform) and was found to be identical to a sample of 17α-ethynyl-19-nor-testosterone prepared according to a different method.

EXAMPLE VI

Preparation of 17α-ethyl-19-nor-testosterone

Step A: Preparation of 3,5-bis-(ethylenedioxy)-17α-ethyl-4,5-seco-estrane-17β-ol 30 cc of toluene and 15 cc of ethanol containing 0.2% of pyridine were introduced into a hydrogenation vessel, then 3 gm of 3,5-bis-(ethylenedioxy)-17α-ethynyl-4,5-seco-estrane-17β-ol (described in Step A of Example V) and finally 1.2 gm of palladized talc containing 2% of palladium were added. The apparatus was purged, and the mixture therein was agitated under an atmosphere of hydrogen until the completion of absorption of the latter. Thereafter the reaction mixture was maintained under agitation for 15 minutes and then the reaction suspension was filtered. The filtrate was distilled to dryness under reduced pressure, obtaining 3.22 gm of raw 3,5-bis-(ethylenedioxy)-17α-ethyl-4,5-seco-estrane-17β-ol which product was utilized as such for the next step.

This product is not described in the literature.

Step B: Preparation of 17α-ethyl-4,5-seco-estrane-17β-ol-3,5-dione 2.13 gm of raw 3,5-bis-(ethylenedioxy)-17α-ethyl-4,5-seco-estrane-17β-ol were dissolved in a mixture of 10.7 cc of toluene, 4.3 cc of methanol and 4.3 cc of water. The solution was heated to reflux and 2.13 gm of citric acid monohydrate were added. Then the solution was maintained at reflux for one hour; thereafter 10.7 cc of water were added. Next, the solution was concentrated under reduced pressure in order to eliminate the toluene and the methanol. The product obtained was extracted with methylene chloride. The methylene chloride solution was dried over magnesium sulfate, distilled to dryness under vacuum, thereby obtaining 1.55 gm of raw 17α-ethyl-4,5-seco-estrane-17β-ol-3,5-dione, which was utilized as such for the next step.

| Infrared spectra (in chloroform): | | |
|---|---|---|
| Absorption at: | 1,358 cm$^{-1}$: | —C—CH$_3$ |
| | | O |
| | 1,708 cm$^{-1}$: | carbonyl |
| | 3,600 cm$^{-1}$: | hydroxyl |

This product is not described in the literature.

Step C: Obtention of 17α-ethyl-19-nor-testosterone 1.35 gm of 17α-ethyl-4,5-seco-estrane-17β-ol-3,5-dione were dissolved in 7 cc of methanol, and 0.236 gm of sodium methylate were added thereto. Next, the solution was agitated for 5 hours at room temperature and thereafter neutralized by the addition of acetic acid. The methanol was distilled therefrom under reduced pressure. Water was added and the insoluble portion of the reaction mixture was extracted with methylene chloride. The methylene chloride solution was dried over magnesium sulfate and concentrated to dryness under reduced pressure. The resultant residue was purified by trituration with ethyl ether, and 0.557 gm of 17α-ethyl-19-nor-testosterone was obtained. The product had a melting point of 136°C and a specific rotation of $[\alpha]_D^{20} = +21° \pm 0.5°$ (c = 2% in methanol).

| Ultraviolet spectra (in ethanol) | |
|---|---|
| max. at 240 to 241 mµ | ε = 16,450 |

This product was identical to 17α-ethyl-19-nor-testosterone prepared according to a different method.

EXAMPLE VII

Preparation of the acetate of 17α-ethynyl-19-nor-testosterone

Step A: Preparation of 3,5-bis-(ethylenedioxy)-17α-ethynyl-17β-acetoxy-4,5-seco-estrane 4 gm of 3,5-bis-(ethylenedioxy)-17α-ethynyl-4,5-seco-estrane-17β-ol (described in Step A of Example V) were introduced into a mixture of 8 cc of pyridine and 4 cc of acetic acid anhydride and heated at 100° to 105°C for 24 hours. Thereafter, the reaction solution was poured into a water-ice mixture. The precipitate formed was vacuum filtered, washed with water and dried. This raw product was purified by trituration with methanol. The product obtained after purification with methanol was dissolved in methylene chloride and agitated with magnesium silicate. The methylene chloride solution was filtered and concentrated to dryness under reduced pressure, thereby obtaining 3.53 gm of 3,5-bis-(ethylenedioxy)-17α-ethynyl-17β-acetoxy-4,5-seco-estrane. The product had a melting point of 174°C and was utilized as such for the next step.

A sample of this product, purified for analysis by crystallization from methanol, had a melting point of 174°C and a specific rotation $[\alpha]_D^{20} = -31.5° \pm 1°$ (c = 1% in chloroform containing 1% of pyridine) and possessed the following characteristics:

Analysis: $C_{26}H_{38}O_6$; molecular weight = 446.56. Calculated: C, 69.92%; H, 8.59%. Found: C, 69.9%; H, 8.8%.

| Infrared spectra (in chloroform): | | |
|---|---|---|
| Absorption at: | 1,738 cm$^{-1}$: | carbonyl |
| | 3,300 cm$^{-1}$: | ethynyl |

This product is not described in the literature.

Step B: Preparation of 17α-ethynyl-17β-acetoxy-4,5-seco-estrane-3,5-dione 3.2 gm of 3,5-bis-(ethylenedioxy)-17α-ethynyl-17β-acetoxy-4,5-seco-estrane were introduced into a mixture of 16 cc of toluene, 6.4 cc of methanol and 6.4 cc of water. Then the reaction mixture was heated to reflux, 3.2 gm of citric acid monohydrate were added, and the reaction mixture was maintained at reflux for 15 hours. Thereafter, 16 cc of water were added to the reaction mixture, which was then distilled under reduced pressure in order to eliminate the toluene and the methanol. After the precipitate obtained had been vacuum filtered and dried, 2.58 gm of a product were recovered which, after crystallization from methanol, supplied 2.2 gm of 17α-ethynyl-17β-acetoxy-4,5-seco-estrane-3,5-dione. The product had a melting point of 170°C. and it was utilized as such for the next step.

A sample of this product, purified for analysis by crystallization from methanol, had a melting point of 170°C. and a specific rotation of $[\alpha]_D^{20} = -58°$ (c = 1% in chloroform) and showed the following characteristics:

Analysis: $C_{22}H_{30}O_4$; molecular weight = 358.46. Calculated: C, 73.71%; H, 8.43%. Found: C, 73.4%; H, 8.3%.

| Infrared spectra (in chloroform): | | |
|---|---|---|
| Absorption at: | 1,708 cm$^{-1}$: | carbonyl |
| | 1,738 cm$^{-1}$: | carbonyl of the acetate |
| | 3,300 cm$^{-1}$: | ethynyl |

This product is not described in the literature.

Step C: Preparation of the 3-pyrrolidyl-17α-ethynyl-17β-acetoxy-Δ$^{3,5}$-estradiene 0.500 gm of 17α-ethynyl-17β-acetoxy-4,5-seco-estrane-3,5-dione were introduced into 5 cc of methanol; then 0.25 cc of pyrrolidine were added. The mixture was agitated for 15 hours at room temperature and under an atmosphere of nitrogen. The precipitate formed was vacuum filtered and washed with methanol, thus obtaining 0.52 gm of 3-pyrrolidyl-17α-ethynyl-17β-acetoxy-Δ$^{3,5}$-estradiene. The product had a melting point of 186°C and a specific rotation $[\alpha]_D^{20} = -276° \pm 4°$ (c = 0.5% in dimethylformamide). It was utilized as such for the next step.

Analysis: $C_{26}H_{35}O_2N$; molecular weight = 393.55. Calculated: C, 79.34%; H, 8.96%; N, 3.56%. Found: C, 79.1%, H, 9.2%; N, 3.9%.

This product is not described in the literature.

Step D: Preparation of the acetate of 17α-ethynyl-19-nor-testosterone 0.285 gm of 3-pyrrolidyl-17α-ethynyl-17β-acetoxy-Δ$^{3,5}$-estradiene were introduced into 1.4 cc of 2 N sulfuric acid. The mixture was agitated for 15 hours at room temperature; then it was slowly poured into a mixture of 2.8 cc of 2N sodium hydroxide solution and 5.7 gm of water and ice. Next, the reaction mixture was again agitated for 2 hours at 0°C., acidified with 9N sulfuric acid to obtain a pH of 1, and then again agitated for 1 hour at 0°C. The precipitate formed was vacuum filtered, washed with water and dried. This product was twice recrystallized from a water-acetone mixture. 0.154 gm of acetate of 17α-ethynyl-19-nor-testosterone was obtained. The product had a melting point of 163°C and a specific rotation $[\alpha]_D^{20} = -28.5° \pm 1\%$ (c = 1% in chloroform). It was identical to a sample of the acetate of 17α-ethynyl-19-nor-testosterone prepared according to a different process.

EXAMPLE VIII

Preparation of 17α-ethynyl-Δ$^{4,9}$-estradiene-17β-ol-3-one

Step A: Preparation of 3,5-bis-(ethylenedioxy)-17α-ethynyl-4,5-seco-Δ$^{9(10)}$-estrene-17β-ol Under an atmosphere of nitrogen, 2.6 gm of potassium were introduced into a mixture of 26.4 cc of tert.-amyl alcohol and 10.4 cc of benzene. The mixture was heated to 55° to 60°C and maintained at this temperature for one hour while agitating. Then a stream of acetylene was allowed to bubble through the reaction solution for 1 hour and 30 minutes at a temperature of 55° to 60°C. Thereafter, the reaction solution was cooled to room temperature and, while maintaining the bubbling of acetylene therethrough, a solution of 500 mg of 3,5-bis-(ethylenedioxy)-4,5-seco-Δ$^{9(10)}$-estrene-17-one (described in Step C of Example IV) in a mixture of 10.4 cc of benzene and 10.4 cc of ethyl ether was introduced into the reaction solution. The reaction mixture was then agitated for two hours while acetylene continued to be bubbled therethrough. Next, water was added to the reaction mixture. The organic phase was separated by decanting, washed with water, dried and concentrated to dryness under reduced pressure.

The residue was triturated with isopropyl ether and then crystallized from the same solvent. In this manner 350 mg of 3,5-bis-(ethylenedioxy)-17α-ethynyl-4,5-seco-Δ$^{9(10)}$-estrene-17β-ol were obtained, having a melting point of 152°C.

A sample of this product was purified for analysis by crystallization first from isopropyl ether, then from aqueous methanol. The product had a melting point of 152°C with a specific rotation $[\alpha]_D^{20} = -21.5°$ (c = 0.5% in methanol).

Analysis: $C_{24}H_{34}O_5$; molecular weight = 402.51. Calculated: C, 71.61%; H, 8.51%. Found: C, 71.5%; H, 8.4.

This product is not described in the literature.

Step B: Preparation of 17α-ethynyl-4,5-seco-Δ$^9$-estrene-17β-ol-3,5-dione

Under an atmosphere of nitrogen, 6 gm of 3,5-bis-(ethylenedioxy)-17α-ethynyl-4,5-seco-Δ$^{9(10)}$-estrene-17β-ol were introduced into a mixture of 30 cc of toluene and 12 cc of methanol. Then 12 cc of water were added to the mixture, which was then brought to reflux while agitating. 6 gm of citric acid were added and the reaction mixture was maintained at reflux for 1 hour. Thereafter, 30 cc of water were added and the methanol and toluene were eliminated under reduced pressure. The aqueous phase was extracted with methylene chloride. The extracts were combined and the organic solution obtained was washed with water, dried and finally concentrated to dryness under reduced pressure.

The residue was admixed with ether. The precipitate formed was isolated by being vacuum filtered, and the mother liquors, which will be referred to hereinafter as "Solution A", were preserved. The product obtained was purified by crystallization from ether and 0.99 gm of 17α-ethynyl-4,5-seco-Δ$^9$-estrene-17β-ol-3,5-dione was obtained having a melting point of 124°C.

A sample of this product was recrystallized from ether and had a melting point of 124°C with a specific rotation $[\alpha]_D^{20} = -73°$ (c = 0.65% in methanol).

Analysis: $C_{20}H_{26}O_3$; molecular weight = 314.41. Calculated: C, 76.40%; H, 8.33%. Found: C, 76.2%; H, 8.4%.

Ultraviolet spectra (in ethanol):

λ max. at 248 to 249 mμ ε = 15,000

This product is not described in the literature.
Moreover, by starting with the "Solution A" maintained at 0°C for several hours, a precipitate was obtained. This precipitate was vacuum filtered and purified by crystallization from ethyl ether. In this manner, 210 mg of 17α-ethynyl-4,5-seco-Δ$^{9(11)}$-estrene-17β-ol-3,5-dione were obtained. The product had a melting point of 143°C and a specific rotation $[\alpha]_D^{20} = -15°$ (c = 0.55% in methanol).

Analysis: $C_{20}H_{26}O_3$; molecular weight = 314.41. Calculated: C, 76.40%; H, 8.33%. Found: C, 76.4%; H, 8.2%.

By employing the conventional processes of ketalization, this compound was converted into 3,5-bis-(ethylenedioxy)-17α-ethynyl-4,5-seco-Δ$^{9(11)}$-estrene-17β-ol, which could be utilized again.

This product is not described in the literature.

Step C: Preparation of 17α-ethynyl-Δ$^{4,9}$-estradiene-17β-ol-3-one

Under an inert atmosphere, 0.600 gm of 17α-ethynyl-4,5-seco-Δ$^9$-estrene-17β-ol-3,5-dione were introduced into 2.2 cc of benzene. Then, while maintaining the temperature between 0° and +3°C., 1.4 cc of a solution of sodium tert.-amylate in toluene, containing 2.45 gm of sodium per 100 cc, was added in the space of 20 minutes. While maintaining the previously recited temperature, the reaction mixture was agitated for 2 hours. Thereafter, first 1 cc of benzene, then a mixture of 0.3 cc of tert.-butyl alcohol and 0.5 cc of benzene were added to the reaction mixture. The temperature was elevated to 20°C and the reaction mixture was agitated for one hour at this temperature. The pH was adjusted to 7 by the addition of a benzenic solution of acetic acid. Next, the reaction mixture was agitated for 45 minutes and then water was added. The solvents were eliminated under reduced pressure. The precipitate formed was vacuum filtered, washed and dried. 570 mg of product were obtained, having a melting point of 178°C.

This product was purified by crystallization from ethyl acetate, thus obtaining 416 mg of 17α-ethynyl-Δ$^{4,9}$-estradiene-17β-ol-3-one. The product had a melting point of 183°C and a specific rotation $[\alpha]_D^{20} = -355°$ (c = 0.2% in methanol).

| Ultraviolet spectra (in ethanol): | |
|---|---|
| max at 125 mμ | ε = 5,850 |
| Inflection toward 235 to 236 mμ | ε = 4,590 |
| Inflection toward 247 mμ | ε = 3,550 |
| max at 340 mμ | ε = 20,000 |

The preceding specific embodiments are illustrative of the process of the invention. It is to be understood, however, that other expedients known to those skilled in the art can be employed without departing from the spirit of the invention or the scope of the appended claims.

We claim:

1. 13β-alkyl-17α-R$^{ir}$-17β-OR-4,5-seco-gonane-3,5-diones of the formula

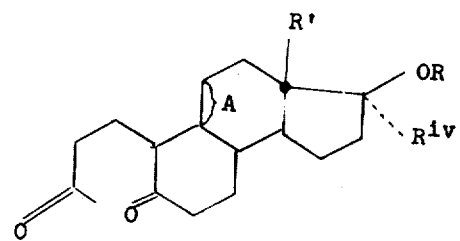

wherein R is a member selected from the group consisting of hydrogen and the acyl of an organic carboxylic acid having from 1 to 18 carbon atoms selected from the group consisting of alkanoic acids, alkenoic acids, cycloalkylcarboxylic acids, cycloalkyl-alkanoic acids, phenylalkanoic acids, phenoxyalkanoic acids, and β-ketoalkanoic acids, R' represents an alkyl having from 1 to 4 carbon atoms, R$^{ir}$ is a member selected from the group consisting of lower alkenyl and lower alkynyl, and A is selected from the group consisting of two hydrogens and a double bond.

2. The compound of claim 1 wherein R is hydrogen, R' is methyl, R$^{ir}$ is ethynyl and A is two hydrogens.

3. The compound of claim 1 wherein R is acetoxy, R' is methyl, R$^{ir}$ is ethynyl and A is two hydrogens.

4. The compound of claim 1 wherein R is hydrogen, R' is methyl, R$^{ir}$ is ethynyl and A is a double bond.

* * * * *